United States Patent [19]

Rosenberger

[11] Patent Number: 4,532,059
[45] Date of Patent: Jul. 30, 1985

[54] BENZYLATED PHENOLS

[75] Inventor: Siegfried Rosenberger, Riehen, Switzerland

[73] Assignee: Ciba-Geigy Corporation, Ardsley, N.Y.

[21] Appl. No.: 552,644

[22] Filed: Nov. 17, 1983

[30] Foreign Application Priority Data

Nov. 25, 1982 [CH] Switzerland .......................... 6875/82

[51] Int. Cl.³ ................................................ C10M 1/20
[52] U.S. Cl. ..................... 252/52 R; 568/720
[58] Field of Search ...................... 252/52 R; 568/720

[56] References Cited

U.S. PATENT DOCUMENTS 3,346,648 10/1967 Worrel ................................. 260/611
4,222,884 9/1980 Malec ................................. 252/52 R
4,278,554 7/1981 Malec ................................. 252/52 R

FOREIGN PATENT DOCUMENTS 253543 8/1964 Australia ............................. 568/720
81457 6/1983 European Pat. Off. .
2138839 3/1972 Fed. Rep. of Germany .
6940583 5/1973 Japan .
1555728 11/1979 United Kingdom .

OTHER PUBLICATIONS

Scott, "Developments in Polymer Stabilization", (1981), pp. 149-163.
Budzikiewicz et al., Chem. Ber. 98, 3264-3269 (1965).

Primary Examiner—William R. Dixon, Jr.
Assistant Examiner—C. Johnson
Attorney, Agent, or Firm—Harry Falber

[57] ABSTRACT

Compounds of the formula

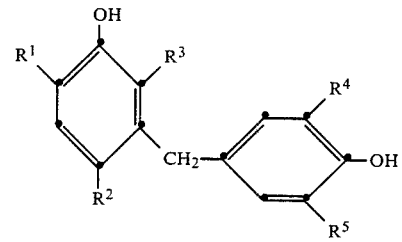

in which $R^1$, $R^2$, $R^3$, $R^4$ and $R^5$ are as defined in the main claim, are suitable for use as stabilizers for organic material, such as polymers or lubricants. In addition to high activity, they are distinguished, in particular, by good color behavior and good compatibility with the substrates to be protected.

9 Claims, No Drawings

BENZYLATED PHENOLS

The present invention relates to phenols which are dibenzylated in the ortho- and meta-positions or in the para- and meta-positions, to their preparation and to their use as stabilisers for organic material, and also to organic material which has been stabilised with their aid.

Benzylated phenols are described in the publication by H. Budzikiewicz and J. Swoboda in Chem. Ber. 98 (10), 3264 (1965), without reference being made to the possibility of their use. Benzylated phenols have also been described as antioxidants, for example in U.S. Pat. No. 3,346,648, German Offenlegungsschrift No. 2,138,839 or Japanese Patent Application No. 69-40,583.

However, the known compounds do not satisfy in every respect the high requirements set for a high-grade stabiliser. As antioxidants, the ortho/meta-benzylated or para/metabenzylated phenols according to the invention show an improved activity, together with an excellent colour behaviour and compatibility with the substrates to be protected.

The invention relates to compounds of the general formula I

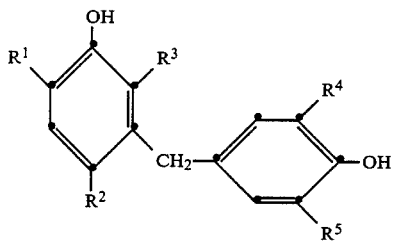

in which one of the radicals $R^1$ and $R^2$ is a group of the formula II

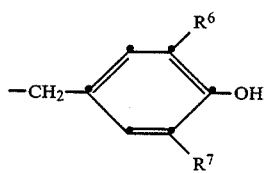

and the other is methyl, and $R^3$, $R^4$, $R^5$, $R^6$ and $R^7$ independently of one another are $C_1$-$C_{12}$-alkyl, $C_5$-$C_8$-cycloalkyl, phenyl, naphthyl, $C_7$-$C_9$-aralkyl or $C_7$-$C_{10}$-alkaryl.

If $R^3$, $R^4$, $R^5$, $R^6$ and $R^7$ are $C_1$-$C_{12}$-alkyl, preferably $C_1$-$C_4$-alkyl, they can be, for example, methyl, ethyl, n-propyl, isopropyl, n-butyl, sec.-butyl, tert.-butyl, isobutyl, n-pentyl, tert.-amyl, n-hexyl, n-octyl, 1,1,3,3-tetramethylbutyl, 2-ethylhexyl or linear or branched nonyl, decyl, undecyl or dodecyl. Preferably, $R^4$ and $R^6$ are methyl or tert.-butyl, and $R^5$ and $R^7$ are tert.-butyl. $R^3$ is preferably methyl.

Examples of $R^3$, $R^4$, $R^5$, $R^6$ and $R^7$ as $C_5$-$C_8$-cycloalkyl are cyclopentyl, cycloheptyl, cyclooctyl and, preferably, cyclohexyl.

If the substituents $R^3$, $R^4$, $R^5$, $R^6$ and $R^7$ are $C_7$-$C_{10}$-aralkyl, they are, for example, benzyl, 1-phenylethyl, α,α-dimethylbenzyl or 2-phenylethyl.

Examples of $R^3$, $R^4$, $R^5$, $R^6$ and $R^7$ as $C_7$-$C_{10}$-alkaryl are o-tolyl, m-tolyl, p-tolyl, 2,4-dimethylphenyl, 2,6-dimethylphenyl, 2,6-diethylphenyl or 4-tert.-butylphenyl. 2,4-dimethylphenyl is preferred.

In preferred compounds, the substituents $R^4$ and $R^6$ or $R^5$ and $R^7$ have the same meaning.

Preferred compounds of the formula I are those in which one of the radicals $R^1$ and $R^2$ is a group of the formula III

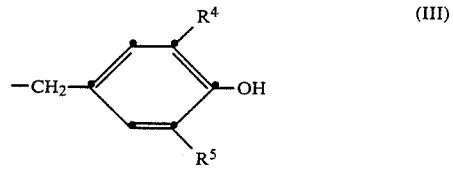

and the other is methyl, and $R^3$, $R^4$ and $R^5$ independently of one another are $C_1$-$C_4$-alkyl, cyclohexyl, phenyl, $C_7$-$C_9$-aralkyl or $C_7$-$C_{10}$-alkaryl.

Compounds of the formula I which are particularly preferred are those in which one of the radicals $R^1$ and $R^2$ is a group of the formula III and the other is methyl, and $R^3$, $R^4$ and $R^5$ independently of one another are $C_1$-$C_4$-alkyl.

Compounds of the formula I which are of particular interest are those in which one of the radicals $R^1$ and $R^2$ is a group of the formula III and the other is methyl, $R^3$ is $C_1$-$C_4$-alkyl, $R^4$ is methyl or t.-butyl and $R^5$ is tert.-butyl.

The following are examples of compounds of the formula I: 2,6-dimethyl-3,4-di-(3',5'-di-tert.-butyl-4'-hydroxybenzyl)-phenol, 2,4-dimethyl-3,6-di-(3',5'-di-tert.-butyl-4'-hydroxybenzyl)-phenol, 2,6,-dimethyl-3,4-di-(3'-methyl-5'-tert.-butyl-4'-hydroxybenzyl)-phenol, 2,4-dimethyl-3,6-di-(3'-methyl-5'-tert.-butyl-4'-hydroxybenzyl)-phenol, 2,6-dimethyl-3-(3',5'-di-tert.-butyl-4'-hydroxybenzyl)-4-(3'-methyl-5'-tert.-butyl-4'-hydroxybenzyl)-phenol, 2,6-dimethyl-3-(3'-methyl-5'-tert.-butyl-4'-hydroxybenzyl)-3-(3',5'-di-tert.-butyl-4'-hydroxybenzyl)-phenol, 2,4-dimethyl-3-(3',5'-di-tert.-butyl-4'-hydroxybenzyl)-6-(3'-methyl-5'-tert.-butyl-4'-hydroxybenzyl)-phenol, 2,4-dimethyl-3-(3'-methyl-5'-tert.-butyl-4'-hydroxybenzyl)-6-(3',5'-di-tert.-butyl-4'-hydroxybenzyl)-phenol, 2-ethyl-6-methyl-3,4-di-(3',5'-di-tert.-butyl-4'-hydroxybenzyl)-phenol, 2-butyl-4-methyl-3,6-di-(3',5'-di-tert.-butyl-4'-hydroxybenzyl)-phenol, 2,6-dimethyl-3,4-di-(3',5'-dicyclohexyl-4'-hydroxybenzyl)-phenol and 2,6-dimethyl-3,4-di-(3',5'-dibenzyl-4'-hydroxybenzyl)-phenol.

The compounds of the formula I are prepared by benzylation reactions which are known per se. This is effected, for example, by reacting approximately one mole of a phenol of the formula IV or V

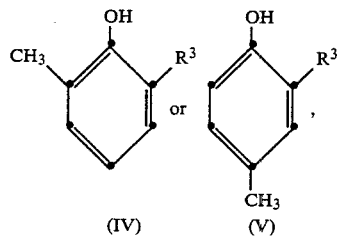

in which $R^3$ is as defined above, with approximately one mole of a benzylation component of the formula VI

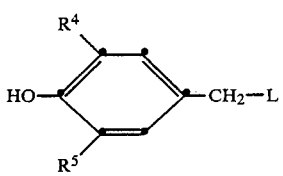

(VI)

and approximately one mole of a benzylation component of the formula VII

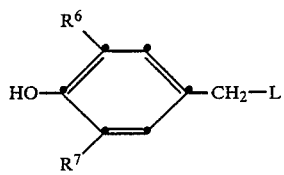

in which L is hydroxyl, $C_1$-$C_4$-alkoxy or di-($C_1$-$C_4$)-alkylamino and $R^4$, $R^5$, $R^6$ and $R^7$ are as defined above.

The reactions can, if desired, be carried out in the presence of bases (for example tertiary amines; hydroxides, amides or carbonates of alkali or alkaline earth metals), but can also be carried out, if desired, in the presence of acid catalysts (such as $H_2SO_4$, HCl, p-toluenesulfonic acid, $BF_3$-etherate, $ZnCl_2$, $CaCl_2$ or $AlCl_3$.

The process can be carried out with or without a solvent. If a solvent is used, it is an inert solvent, such as alkanes (for example hexane, petroleum ether or white spirit), aromatic hydrocarbons (for example benzene, toluene or xylene), ethers (such as diethyl ether, diisopropyl ether or dibutyl ether), dimethylformamide, dimethylacetamide or dioxane. In addition, alcohols (such as methanol, isopropanol or butanol) and chloroalkanes (such as methylene chloride) are also suitable as solvents.

The reaction can be carried out at temperatures between 20° and 160° C. The upper limit is preferably set by the reflux temperature of the solvent selected.

The starting materials of the formulae IV, V, VI and VII are known substances, the preparation of which is familiar to those skilled in the art. Amongst them are various commercially available compounds.

The invention also relates to the use of the compounds of the formula I as stabilisers for organic material to protect the latter against damage caused by the action of oxygen, heat, light and high-energy radiation, for example $\beta$-radiation and $\gamma$-radiation.

Preferred forms of this use in accordance with the invention are the use of the compounds as stabilisers in organic polymers, particularly in graft polymers based on acrylonitrile, butadiene and styrene (ABS) or in impact-resistant polystyrene.

The following are further examples of organic material which can be stabilized advantageously by means of the compounds according to the invention:

1. Polymers of monoolefins and diolefins, for example polyethylene (which can, if desired, be crosslinked), polypropylene, polyisobutylene, polybut-1-ene, polymethylpent-1-ene, polyisoprene or polybutadiene and also polymers of cycloolefins, for example cyclopentene or norbornene.
2. Mixtures of the polymers mentioned under (1), for example mixtures of polypropylene with polyethylene or with polyisobutylene.
3. Copolymers of monoolefins and diolefins with one another or with other vinyl monomers, for instance ethylene/propylene copolymers, propylene/but-1-ene copolymers, propylene/isobutylene copolymers, ethylene/but-1-ene copolymers, propylene/butadiene copolymers, isobutylene/isoprene copolymers, ethylene/alkyl acrylate copolymers, ethylene/alkyl methacrylate copolymers, ethylene/vinyl acetate copolymers or ethylene/acrylic acid copolymers and salts thereof (ionomers), and also terpolymers of ethylene with propylene and a diene, such as hexadiene, dicyclopentadiene or ethylidenenorbornene.
4. Polystyrene.
5. Copolymers of polystyrene or α-methylstyrene with dienes or acrylic derivatives, for example styrene/butadiene or styrene/acrylonitrile/methyl acrylate; mixtures of high impact strength obtained from styrene copolymers and another polymer for example a polyacrylate, a diene polymer or an ethylene/propylene/diene terpolymer; and also block copolymers of styrene, for example styrene/butadiene/styrene, styrene/isoprene/styrene, styrene/ethylene-butylene/styrene or styrene/ethylene-propylene/styrene.
6. Graft copolymers of styrene, for example styrene on polybutadiene, styrene and acrylonitrile on polybutadiene, styrene and maleic anhydride on polybutadiene, styrene and alkyl acrylates or alkyl methacrylates on polybutadiene, styrene and acrylonitrile on ethylene/propylene/diene terpolymers, styrene and acrylonitrile on polyalkyl acrylates or polyalkyl methacrylates, styrene and acrylonitrile on acrylate/butadiene copolymers and mixtures thereof with the copolymers mentioned under (5), such as those known as ABS, MBS or AES polymers.
7. Halogen-containing polymers, for example polychloroprene, chlorinated rubber, chlorinated or chlorosulfonated polyethylene, epichlorohydrin homopolymers and copolymers and especially polymers obtained from halogen-containing vinyl compounds, for example polyvinyl chloride, polyvinylidene chloride, polyvinyl fluoride or polyvinylidene fluoride; and copolymers thereof, such as vinyl chloride/vinylidene chloride, vinyl chloride/vinyl acetate or vinylidene chloride/vinyl acetate.
8. Polymers derived from α,β-unsaturated acids and derivatives thereof, such as polyacrylates and polymethacrylates, polyacrylamides and polyacrylonitriles.
9. Copolymers of the monomers mentioned under (8) with one another or with other unsaturated monomers, for example acrylonitrile/butadiene copolymers, acrylonitrile/alkyl acrylate copolymers, acrylonitrile/alkoxyalkyl acrylate copolymers, acrylonitrile/vinyl halide copolymers or acrylonitrile/alkyl methacrylate/butadiene terpolymers.
10. Polymers derived from unsaturated alcohols and amines or acyl derivatives or acetals thereof, such as polyvinyl alcohol, polyvinyl acetate, stearate, benzoate or maleate, polyvinyl butyral, polyallyl phthalate or polyallylmelamine.
11. Homopolymers and copolymers of cyclic ethers, such as polyalkylene glycols, polyethylene oxide, polypropylene oxide or copolymers thereof with bisglycidyl ethers.
12. Polyacetals, such as polyoxymethylene, and also polyoxymethylenes containing comonomers, for example ethylene oxide.

13. Polyphenylene oxides and sulfides and mixtures of polyphenylene oxides with polystyrene.
14. Polyurethanes derived on the one hand from polyethers, polyesters and polybutadienes containing terminal hydroxyl groups and, on the other hand, from aliphatic or aromatic polyisocyanates, and also precursors thereof (polyisocyanates, polyols and prepolymers).
15. Polyamides and copolyamides derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethyleneterephthalamide, poly-m-phenyleneisophthalamide and copolymers thereof with polyethers, for example polyethylene glycol, polypropylene glycol or polytetramethylene glycol.
16. Polyureas, polyimides and polyamide-imides.
17. Polyesters derived from dicarboxylic acids and diols and/or from hydroxycarboxylic acids or the corresponding lactones, such as polyethylene terephthalate, polybutylene terephthalate, poly-1,4-dimethylolcyclohexane terephthalate, poly-[2,2-bis(4-hydroxyphenyl)-propane]terephthlate, polyhydroxybenzoates, and block polyether-esters derived from polyethylene containing hydroxyl groups, dialcohols and dicarboxylic acids.
18. Polycarbonates.
19. Polysulfones and polyether-sulfones.
20. Crosslinked polymers derived on the one hand from aldehydes and, on the other hand, from phenols, urea or melamine, such as phenol-formaldehyde resins, urea-formaldehyde resins and melamine-formaldehyde resins.
21. Drying and non-drying alkyd resins.
22. Unsaturated polyester resins derived from copolyesters of saturated and unsaturated dicarboxylic acids with polyhydric alcohols, and also vinyl compounds as crosslinking agents, and also halogen-containing modifications thereof of low combustibility.
23. Crosslinkable acrylic resins derived from substituted acrylic acid esters, for example epoxy-acrylates, urethaneacrylates or polyester-acrylates.
24. Alkyd resins, polyester resins and acrylate resins which have been crosslinked with melamine resins, urea resins, polyisocyanates or epoxide resins.
25. Crosslinked epoxide resins derived from polyepoxides, for example bisglycidyl ethers or cycloaliphatic diepoxides.
26. Natural polymers, such as cellulose, natural rubber and gelatin and also polymer-homologously chemically modified derivatives thereof, such as cellulose acetates, propionates and butyrates, and the cellulose ethers, such as methylcellulose.
27. Natural and synthetic organic substances which constitute pure monomeric compounds or mixtures thereof, for example mineral oils, animal and vegetable fats, oils and waxes, or oils, waxes and fats based on synthetic esters (for example phthalates, adipates, phosphates or trimellitates) and also mixtures of synthetic esters with mineral oils in any desired ratios by weight, such as are used, for example, as plasticisers for plastics or as spinning dressings, and aqueous emulsions thereof.
28. Aqueous emulsions of natural or synthetic rubbers, for example natural rubber latex or latices of carboxylated styrene/butadiene copolymers.

The stabilisation of styrene polymers and elastomers, especially ABS, is of particular importance. The polymers which have been stabilised in accordance with the invention display an excellent colour behaviour, and these stabilisers have optimum compatibility with the polymers.

The compounds, according to the invention, of the formula I are also particularly suitable for use as stabilisers for lubricants.

The stabilisers are added in a concentration of 0.01 to 5% by weight, calculated on the material to be stabilised. It is advantageous to incorporate into the material to be stabilised 0.1 to 2.0, particularly preferentially 0.2 to 0.6, % by weight of the compounds, calculated on the material.

The incorporation can be effected after polymerisation, for example by mixing the compounds and, if desired, further additives into the melt in accordance with the methods customary in the state of the art, before or during shaping, or by applying the compounds, dissolved or dispersed, to the polymer, if desired with subsequent evaporation of the solvent.

The invention also relate, therefore, to the organic material which has been stabilised by the addition of 0.01 to 5% by weight of a compound of the formula I, and which can, if desired, also contain other known and customary additives. The material thus stabilised can be used in a very wide variety of forms, for example as sheets, fibres, tapes or sections, or as binders for paints, adhesives or cements.

The following should be mentioned as examples of further additives together with which the stabilisers which can be used in accordance with the invention can be employed:

1. Antioxidants 1.1. Alkylated monophenols 2,6-Di-tert.-butyl-4-methylphenol, 2-tert.-butyl-4,6-dimethylphenol, 2,6-di-tert.-butyl-4-ethylphenol, 2,6-di-tert.-butyl-4-n-butylphenol, 2,6-di-tert.-butyl-4-i-butylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert.-butyl-4-methoxymethylphenol and 2,6-diphenyl-4-octadecyloxyphenol.

1.2. Alkylated hydroquinones 2,6-Di-tert.-butyl-4-methoxyphenol, 2,5-di-tert.-butyl hydroquinone and 2,5-di-tert.-amyl hydroquinone.

1.3. Hydroxylated thiodiphenyl ethers 2,2'-Thio-bis-(6-tert.-butyl-4-methylphenol), 2,2'-thio-bis-(4-octylphenol), 4,4'-thio-bis-(6-tert.-butyl-3-methylphenol) and 4,4'-thio-bis-(6-tert.-butyl-2-methylphenol).

1.4. Alkylidene-bisphenols 2,2'-Methylene-bis-(6-tert.-butyl-4-methylphenol), 2,2'-methylene-bis-(6-tert.-butyl-4-ethylphenol), 2,2'-methylene-bis-[4-methyl-6-(α-methylcyclohexyl)-phenol], 2,2'-methylene-bis-(4-methyl-6-cyclohexylphenol), 2,2'-methylene-bis-(6-nonyl-4-methylphenol), 2,2'-methylene-bis-(4,6-di-tert.-butylphenol), 2,2'-ethylidene-bis-(4,6-di-tert.-butylphenol), 2,2'-ethylidene-bis-(6-tert.-butyl-4-isobutylphenol), 4,4'-methylene-bis-(2,6-di-tert.-butylphenol), 4,4'-methylene-bis-(6-tert.-butyl-2-methylphenol), 1,1-bis-(5- tert.-butyl-4-hydroxy-2-methylphenyl)-butane, 2,6-di-(3-tert.-butyl-5-methyl-2-hydroxybenzyl)-4-methylphenol, 1,1,3-tris-(5-tert.-butyl-4-hydroxy-2-methylphenyl)-butane, 1,1-bis-(5-tert.-butyl-4-hydroxy-2-methylphenyl)-3-n-dodecylmercaptobutane, ethylene glycol bis-[3,3-bis-(3'-tert.-butyl-4'-hydroxyphenyl)-butyrate], di-(3-tert.-butyl-4-hydroxy-5-methyl-phenyl)-dicyclopentadiene and di-[2-(3'-tert.-butyl-2'-hydroxy-5'-methylbenzyl)-6-tert.-butyl-4-methylphenyl]terephthalate.

1.5. Benzyl compounds 1,3,5-Tri-(3,5-di-tert.-butyl-4-hydroxybenzyl)-2,4,6-trimethylbenzene, di-(3,5-di-tert.-butyl-4-hydroxybenzyl)sulfide, isooctyl 3,5-di-tert.-butyl-4-hydroxybenzylmercaptoacetate, bis-(4-tert.-butyl-3-hydroxy-2,6-dimethylbenzyl)dithiol terephthalate, 1,3,5-tris-(3,5-di-tert.-butyl-4-hydroxybenzyl) isocyanurate, 1,3,5-tris-(4-tert.-butyl-3-hydroxy-2,6-dimethylbenzyl) isocyanurate, dioctadecyl 3,5-di-tert.-butyl-4-hydroxybenzylphosphonate and the calcium salt of monoethyl 3,5-di-tert.-butyl-4-hydroxybenzylphosphonate.

1.6. Acylaminophenols

4-Hydroxylauranilide, 4-hydroxystearanilide and 2,4-bis-octylmercapto-6-(3,5-di-tert.-butyl-4-hydroxyanilino)-s-triazine.

1.7. Esters of β-(3,5-di-tert.-butyl-4-hydroxyphenyl)-propionic acid with monohydric or polyhydric alcohols, for example methanol, octadecanol, 1,6-hexanediol, neopentylglycol, thiodiethylene glycol, diethylene glycol, triethylene glycol, pentaerythritol, tris-hydroxyethyl isocyanurate and di-hydroxyethyloxalic acid diamide.

1.8. Esters of β-(5-tert.-butyl-4-hydroxy-3-methylphenyl)-propionic acid with monohydric or polyhydric alcohols, for example methanol, octadecanol, 1,6-hexanediol, neopentylglycol, thiodiethylene glycol, diethylene glycol, triethylene glycol, pentaerythritol, tris-hydroxyethyl isocyanurate and di-hydroxyethyloxalic acid diamide.

1.9. Amides of β-(3,5-di-tert.-butyl-4-hydroxyphenyl)-propionic acid, for example N,N'-di-(3,5-di-tert.-butyl-4-hydroxyphenylpropionyl)-hexamethylenediamine, N,N'-di-(3,5-di-tert.-butyl-4-hydroxyphenylpropionyl)-trimethylenediamine and N,N'-di-(3,5-di-tert.-butyl-4-hydroxyphenylpropionyl)-hydrazine.

2. UV absorbers and light stabilisers

2.1. 2-(2'-Hydroxyphenyl)-benztriazole, for example the 5'-methyl-, 3',5'-di-tert.-butyl-, 5'-tert.-butyl-, 5'-(1,1,3,3-tetramethylbutyl)-, 5-chloro-3',5'-di-tert.-butyl-, 5-chloro-3'-tert.-butyl-5'-methyl-, 3'-sec.-butyl-5'-tert.-butyl-, 4'-octoxy- and 3',5'-di-tert.-amyl-derivatives.

2.2. 2-Hydroxybenzophenones, for example the 4-hydroxy-, 4-methoxy-, 4-octoxy-, 4-decyloxy-, 4-dodecyloxy-, 4-benzyloxy-, 4,2',4'-trihydroxy- and 2'-hydroxy-4,4'-dimethoxy-derivatives.

2.3. Esters of substituted or unsubstituted benzoic acids for example 4-tert.-butylphenyl salicylate, phenyl salicylate, octylphenyl salicylate, dibenzoylresorcinol, bis-(4-tert.-butylbenzoyl)-resorcinol, benzoylresorcinol and 2,4-di-tert.-butylphenyl 3,5-di-tert.-butyl-4-hydroxybenzoate.

2.4. Acrylates for example ethyl or isooctyl α-cyano-β,β-diphenylacrylate, methyl α-carbomethoxycinnamate, methyl or butyl α-cyano-β-methyl-p-methoxycinnamate, methyl α-carbomethoxy-p-methoxycinnamate or N-(β-carbomethoxy-β-cyanovinyl)-2-methylindoline.

2.5. Nickel compounds for example nickel complexes of 2,2'-thio-bis-[4-(1,1,3,3-tetramethylbutyl)-phenol], such as the 1:1- or 1:2-complex, which can contain additional ligands, such as n-butylamine, triethanolamine or N-cyclohexyldiethanolamine, nickel dibutyldithiocarbamate, nickel salts of monoalkyl 4-hydroxy-3,5-di-tert.-butylbenzylphosphonates, such as methyl or ethyl ester, nickel complexes of ketoximes, such as 2-hydroxy-4-methylphenyl undecyl ketone oxime and nickel complexes of 1-phenyl-4-lauroyl-5-hydroxypyrazole, which can contain additional ligands.

2.6. Sterically hindered amines for example bis-(2,2,6,6-tetramethylpiperidyl)sebacate, bis-(1,2,2,6,6-pentamethyl-piperidyl)sebacate, bis-(1,2,2,6,6-pentamethylpiperidyl)n-butyl-3,5-di-tert.-butyl-4-hydroxybenzylmalonate, the condensation product formed from 1-hydroxyethyl-2,2,6,6-tetramethyl-4-hydroxypiperidine and succinic acid, the condensation product formed from N,N'-(2,2,6,6-tetramethylpiperidyl)-hexamethylenediamine and 4-tert.-octylamino-2,6-dichloro-1,3,5-s-triazine, and tris-(2,2,6,6-tetramethylpiperidyl)nitrilotriacetate.

2.7. Oxalic acid diamides for example 4,4'-di-octyloxyoxanilide, 2,2'-di-octyloxy-5,5'-di-tert.-butyloxanilide, 2,2'-di-dodecyloxy-5,5'-di-tert.-butyloxanilide, 2-ethoxy-2'-ethyloxanilide, N,N'-bis-(3-dimethylaminopropyl)-oxalamide, 2-ethoxy-5-tert.-butyl-2'-ethyloxanilide and a mixture thereof with 2-ethoxy-2'-ethyl-5,4'-di-tert.-butyloxanilide and mixtures of ortho-methoxy and para-methoxy-substituted oxanilides and of o-ethoxy-disubstituted and p-ethoxy-distributed oxanilides.

3. Metal deactivators for example N,N'-diphenyloxalic acid diamide, N-salicylal-N'-salicyloylhydrazine, N,N'-bissalicyloylhydrazine, N,N'-bis-(3,5-di-tert.-butyl-4-hydroxyphenylpropionyl)-hydrazine, 3-salicyloylamino-1,2,4-triazole and bisbenzylideneoxalic acid dihydrazide.

4. Phosphites and phosphonites for example triphenyl phosphite, diphenylalkyl phosphites, phenyldialkyl phosphites, tri-(nonylphenyl)-phosphite, trilauryl phosphite, trioctadecyl phosphite, distearylpentaerythritol diphosphite, tris-(2,4-di-tert.-butylphenyl)phosphite, diisodecylpentaerythritol diphosphite, di-(2,4-di-tert.-butylphenyl)-pentaerythritol diphosphite, tristearylsorbitol triphosphite and tetrakis-(2,4-di-tert.-butylphenyl)4,4'-biphenylenediphosphonite.

5. Compounds which destroy peroxides for example esters of β-thiodipropionic acid, for example the lauryl, stearyl, myristyl or tridecyl esters, mercaptobenzimidazole, the zinc salt of 2-mercaptobenzimidazole, zinc dibutyldithiocarbamate, dioctadecyl disulfide and pentaerythritol tetrakis-(β-dodecylmercapto)-propionate.

6. Polyamide stabilisers for example copper salts in combination with iodides and/or phosphorus compounds, and salts of divalent manganese.

7. Basic co-stabilisers for example melamine, polyvinylpyrrolidone, dicyandiamide, triallyl cyanurate, urea derivatives, hydrazine derivatives, amines, polyamides, polyurethanes, alkali and alkaline earth metal salts of higher fatty acids, for example Ca stearate, Zn stearate, Mg stearate, Na ricinoleate and K palmitate, antimony pyrocatecholate or tin pyrocatecholate.

8. Nucleating agents for example 4-tert.-butylbenzoic acid, adipic acid and diphenylacetic acid.

9. Fillers and reinforcing agents for example calcium carbonates, silicates, glass fibres, asbestos, talc, kaolin, mica, barium sulfate, metal oxides and hydroxides, carbon black and graphite.

10. Other additives for example plasticisers, lubricants, emulsifiers, pigments, fluorescent brighteners, flame-retarding agents, antistatic agents and blowing agents.

EXAMPLE 1

2,6-Dimethyl-3,4-di-(3',5'-di-t.-butyl-4'-hydroxybenzyl)-phenol 12.2 g of 2,6-dimethylphenol are dissolved in 100 ml of methanol, and 18 g of 80% sulfuric acid are added. 50 g of 4-methoxymethyl-2,6-di-t.-butylphenol are then added in portions at 50° C. in the course of 2 hours in a nitrogen atmosphere and with stirring. The reaction mixture is stirring for 14 hours at 50° C. under a reflux condenser. After being precipitated with water at 20° C., the oily reaction product is then taken up in toluene, the toluene solution is washed with water until neutral and dried with $Na_2SO_4$, and the product of the present example is separated in a pure state by chromatography over a silica gel column[1] from the toluene solution, after the latter has been considerably concentrated. The product solidifies in the form of crystals.

Melting point 155° C.

[1]Merck, Darmstadt: "Kieselgel 60"; particle size 70–230 mesh ASTM.

EXAMPLE 2

The procedure of Example 1 is repeated, except that the isomeric 2,4-dimethylphenol is used instead of 2,4-dimethylphenol is used instead of 2,6-dimethylphenol; an otherwise analogous procedure gives 2,4-dimethyl-3,6-di-(3',5'-di-t.-butyl-4'-hydroxybenzyl)-phenol in the form of colourless crystals of melting point 132° C.

EXAMPLE 3

100 parts by weight of unstabilised ABS powder are mixed with various stabilisers indicated in Tables I and II.

The resulting mixtures are compounded on a two-roll mill for 5 minutes at a maximum temperature of 170° C., and the sheet is then removed. The rough sheet is compressed on a hydraulic laboratory press at 180° C. for 6 minutes to give panels 1 mm thick, from which test specimens of dimensions 50×20 mm are punched out.

The effectiveness of the stabilisers added to the test specimens is tested by heat-ageing in a circulating air oven at 180° C. The criterion used for the damage caused during ageing (oxidation) is the infrared absorption spectrum of the surface, which is obtained by means of reflection spectroscopy (ATR). In particular, the increase in the carbonyl extinction (1,720 $cm^{-1}$) is followed as a function of time, and is compared with a constant absorption band (1,455 $cm^{-1}$). The following is then taken as a measure of the degradation:

$$V = \frac{\text{Optical density at 1,720 } cm^{-1} (> C = O)}{\text{Optical density at 1,455 } cm^{-1} (> CH_2)}$$

The time after which V reaches the value 0.1 ($t_{0.1}$) is taken as an arbitrary end point.

TABLE I

| | Testing in ABS without a synergist. | | | | |
|---|---|---|---|---|---|
| Stabiliser | Oven ageing at 180° C. | | | | |
| according to | | Y.I. ASTM D 1925 | | | |
| Example No. | | after ... minutes of oven ageing | | | |
| 0.25% by weight | $t_{0.1}$ | 0 | 30 | 60 | 90 |
| 1 | 54' | 21 | 31 | 39 | 63 |
| 2 | 65' | 18 | 28 | 35 | 50 |
| without stabiliser | 7' | 17 | 53 | 73 | 83 |

TABLE II

| Testing in ABS together with the synergist DLTDP (dilauryl thiodipropionate). | | | | | | | |
|---|---|---|---|---|---|---|---|
| Stabiliser according to Example No. + DLTDP | | | | | | | |
| 0.25% by weight | OVEN AGEING AT 180° C. | | | | | | |
| of stabiliser | | Y.I. ASTM after ... minutes | | | | | |
| 0.5% by weight of DLTDP | $t_{0.1}$ | 0 | 30 | 60 | 90 | 120 | 150 |
| 1 | 120' | 19 | 29 | 33 | 37 | 41 | 54 |
| 2 | 132' | 18 | 27 | 31 | 35 | 41 | 61 |
| without stabiliser | 7' | 17 | 53 | 73 | 83 | | |

EXAMPLE 4

An impact-resistant polystyrene containing 8% by weight of polybutadiene (high-cis) and containing 0.035% by weight of 2,6-di-tert.-butyl-p-cresol as the main stabiliser, 0.05% by weight of zinc stearate as a lubricant and 0.1% by weight of one of the antioxidants according to the invention (characterised in each of the Tables III and IV below by the number of the corresponding preparation example) is extruded twice at 220° C., and the resulting granules are compressed at 185° C. in the course of 3 minutes to give test panels 2 mm thick.

The test specimens are subjected to oven ageing in a circulating air oven and (a) the Yellowness Index as specified in ASTM D 1925 is determined at 80° C. (test specimens measured after 0, 250, 500, 750 and 1,000 hours) and at 160° C. (test specimens measured after 0, 60, 90, 120 and 180 minutes). The requests are shown in Table III.

(b) The impact strength (IS) in kp. cm/cm² is determined after ageing at 160° C. (test specimens measured after 30, 60, 120, 150, 180, 240, 300, 360, 420 and 480 minutes). The latter results are shown in Table IV.

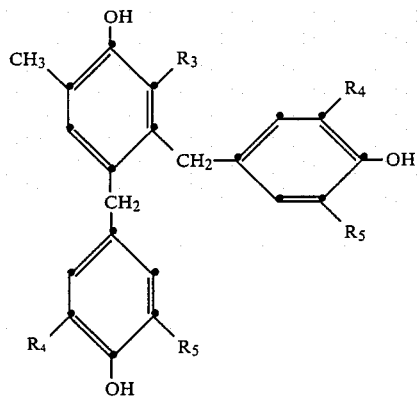

TABLE III

| Stabiliser according to Example No. | Y.I. at 80° C. after ... hours | | | | | Y.I. at 160° C. after ... minutes | | | | |
|---|---|---|---|---|---|---|---|---|---|---|
| | 0 | 250 | 500 | 700 | 1000 | 0 | 60 | 90 | 120 | 180 |
| without stabiliser | 1 | 13 | 17 | 18 | 28 | 1 | 22 | 51 | 69 | 86 |
| 1 | 12 | 21 | 27 | 28 | 32 | 12 | 22 | 28 | 36 | 42 |

TABLE IV

| Stabiliser according to Example No. | IS after ageing at 160° C. after ... minutes | | | | | | | |
|---|---|---|---|---|---|---|---|---|
| | 30 | 60 | 120 | 150 | 180 | 240 | 300 | 360 |
| without stabili- | 10.4 | | | | | | | |
| 1 | X | X | X | X | X | X | X | 10.5 |

X signifies: test specimen not broken.

What is claimed is:
1. A compound of the formula wherein $R_3$, $R_4$ and $R_5$ are $C_1$–$C_4$ alkyl, cyclohexyl, phenyl, $C_7$–$C_9$ aralkyl or $C_7$–$C_{10}$ alkaryl.

2. A compound according to claim 1, of the formula I, in which $R^3$, $R^4$ and $R^5$ independently of one another are $C_1$–$C_4$-alkyl.

3. A compound according to claim 2, of the formula I, in which $R^3$ is $C_1$–$C_4$-alkyl, $R^4$ is methyl or tert.-butyl and $R^5$ is tert.-butyl.

4. The compound 2,6-dimethyl-3,4-di-(3',5'-di-tert.-butyl-4'-hydroxybenzyl)-phenol according to claim 1.

5. The compound 2,4-dimethyl-3,6-di-(3',5'-di-tert.-butyl-4'-hydroxybenzyl)-phenol according to claim 1.

6. A composition of matter, comprising an organic material subject to oxidative, thermal and actinic degradation stabilized, with an effective stabilizing amount of a compound according to claim 1.

7. A composition according to claim 6, wherein the organic material is a synthetic polymer.

8. A composition according to claim 7, wherein the synthetic polymer is polystyrene, or acrylonitrile/-butadiene/styrene graft polymer (ABS).

9. A composition according to claim 6, wherein the organic material is a lubricant.

* * * * *